(12) United States Patent
Browka et al.

(10) Patent No.: US 12,697,430 B2
(45) Date of Patent: Aug. 4, 2026

(54) MICRO-INFUSION DEVICE AND INFUSION SET

(71) Applicant: CareFusion 303, Inc., San Diego, CA (US)

(72) Inventors: Edward Browka, Oneida, NY (US); James Fentress, Creedmoor, NC (US); Lawrence Farhat, Oceanside, CA (US); Robert Vasko, San Diego, CA (US); Theodore Mosler, Raleigh, NC (US); David Foshee, Apex, NC (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 1395 days.

(21) Appl. No.: 17/379,845

(22) Filed: Jul. 19, 2021

(65) Prior Publication Data

US 2021/0338923 A1      Nov. 4, 2021

Related U.S. Application Data

(60) Continuation of application No. 16/393,749, filed on Apr. 24, 2019, now Pat. No. 11,103,635, which is a
(Continued)

(51) Int. Cl.
*A61M 5/14*      (2006.01)
*A61M 5/142*      (2006.01)
(Continued)

(52) U.S. Cl.
CPC .......... *A61M 5/1409* (2013.01); *A61M 5/142* (2013.01); *A61M 5/165* (2013.01);
(Continued)

(58) Field of Classification Search
CPC .... A61M 5/165; A61M 5/1409; A61M 5/142; A61M 5/16881; A61M 39/24;
(Continued)

(56)      References Cited

U.S. PATENT DOCUMENTS 3,993,066 A  *  11/1976  Virag .................. A61M 5/1412
                                                        604/86
4,534,758 A      8/1985  Akers et al.
(Continued)

FOREIGN PATENT DOCUMENTS

CN      101325983 A      12/2008
CN      103071202 A      5/2013
(Continued)

OTHER PUBLICATIONS

Canadian Office Action for Application No. 3012655, dated Mar. 9, 2023, 5 pages.
(Continued)

*Primary Examiner* — Chelsea E Stinson
*Assistant Examiner* — Mark Golovan
(74) *Attorney, Agent, or Firm* — MASCHOFF BRENNAN

(57)      ABSTRACT

Systems and methods of micro-infusion of medical fluids are disclosed. Micro-infusion systems may include a pump, a patient interface, tubing between the pump and the interface, and a micro-infusion device along the tubing. A first portion of the tubing above the micro-infusion device is longer than a second portion of the tubing below the device. The micro-infusion device may include a chamber in-line with the tubing, a first valve between the chamber and the first portion of the tubing, a second valve between the chamber and the second portion of the tubing and a third valve between the chamber and a dump chamber. The second valve may be slidably disposed within the chamber. A
(Continued)

medical fluid may be provided into the chamber that slides the second valve displacing another fluid in the chamber through the third valve into the dump chamber.

20 Claims, 8 Drawing Sheets

Related U.S. Application Data division of application No. 15/414,556, filed on Jan. 24, 2017, now Pat. No. 10,314,966.

(60) Provisional application No. 62/287,840, filed on Jan. 27, 2016.

(51) Int. Cl.

| | |
|---|---|
| *A61M 5/165* | (2006.01) |
| *A61M 5/168* | (2006.01) |
| *A61M 39/24* | (2006.01) |
| *A61M 5/178* | (2006.01) |
| *A61M 5/28* | (2006.01) |
| *A61M 5/315* | (2006.01) |
| *A61M 39/00* | (2006.01) |
| *A61M 39/22* | (2006.01) |

(52) U.S. Cl.
CPC ........ *A61M 5/16881* (2013.01); *A61M 39/24* (2013.01); *A61M 5/16827* (2013.01); *A61M 2005/1787* (2013.01); *A61M 5/284* (2013.01); *A61M 5/31511* (2013.01); *A61M 5/31578* (2013.01); *A61M 5/31596* (2013.01); *A61M 2039/0018* (2013.01); *A61M 39/225* (2013.01); *A61M 2039/242* (2013.01); *A61M 2205/502* (2013.01); *A61M 2205/6054* (2013.01); *A61M 2205/6072* (2013.01); *A61M 2240/00* (2013.01)

(58) Field of Classification Search
CPC .............. A61M 5/284; A61M 5/16827; A61M 5/31511; A61M 5/31578; A61M 5/31596; A61M 39/225; A61M 2005/1787; A61M 2039/0018; A61M 2039/242; A61M 2205/502; A61M 2205/6072; A61M 2205/6054; A61M 2240/00; A61M 5/1408; A61M 5/19; A61M 1/15625; A61M 2039/0211; A61M 2039/0214; A61M 2039/0217; A61M 60/869; A61M 5/2066; G01B 7/003
See application file for complete search history.

(56) References Cited

U.S. PATENT DOCUMENTS

| | | | | |
|---|---|---|---|---|
| 4,834,705 | A | | 5/1989 | Vaillancourt |
| 5,049,129 | A | | 9/1991 | Zdeb et al. |
| 5,267,964 | A | * | 12/1993 | Karg ................... A61M 5/1424 |
| | | | | 604/141 |
| 5,575,779 | A | | 11/1996 | Barry |
| 5,697,904 | A | | 12/1997 | Raines et al. |
| 7,169,128 | B2 | * | 1/2007 | Kriesel ............. A61M 5/16827 |
| | | | | 604/890.1 |
| 7,566,320 | B2 | * | 7/2009 | Duchon ............ A61M 5/14546 |
| | | | | 604/232 |
| 2005/0182383 | A1 | | 8/2005 | Wallen |
| 2005/0234428 | A1 | | 10/2005 | Spohn et al. |
| 2008/0208137 | A1 | * | 8/2008 | Fago .................. A61M 5/31596 |
| | | | | 604/236 |
| 2012/0123298 | A1 | | 5/2012 | Mendels et al. |
| 2012/0185267 | A1 | * | 7/2012 | Kamen ................ A61B 5/0024 |
| | | | | 705/2 |
| 2014/0008366 | A1 | * | 1/2014 | Genosar ................ A61J 1/2096 |
| | | | | 220/265 |
| 2015/0105674 | A1 | | 4/2015 | Spohn et al. |
| 2015/0374910 | A1 | | 12/2015 | Mansour |
| 2015/0374916 | A1 | * | 12/2015 | Bertolote ................ A61M 5/19 |
| | | | | 604/82 |

FOREIGN PATENT DOCUMENTS

| | | |
|---|---|---|
| CN | 104411347 A | 3/2015 |
| CN | 204395138 U | 6/2015 |
| EP | 0100296 | 2/1984 |
| EP | 0355199 A1 | 2/1990 |
| GB | 2492941 A | 1/2013 |
| WO | WO-1993016754 | 9/1993 |
| WO | WO-2005057466 | 6/2005 |

OTHER PUBLICATIONS

Australian Office Action for Application No. 2017212349, dated Nov. 26, 2020, 6 pages.
Chinese Office Action for Application No. 201780010908.2, dated Apr. 22, 2020, 17 pages.
Extended European Search Report for Application No. 19209482.9, dated May 14, 2020, 8 pages.
International Search Report and Written Opinion for Application No. PCT/US2017/014685, dated May 10, 2017, 16 pages.
Chinese Office Action for Application No. 202011576294.4, dated Apr. 14, 2022, 10 pages including translation.

* cited by examiner

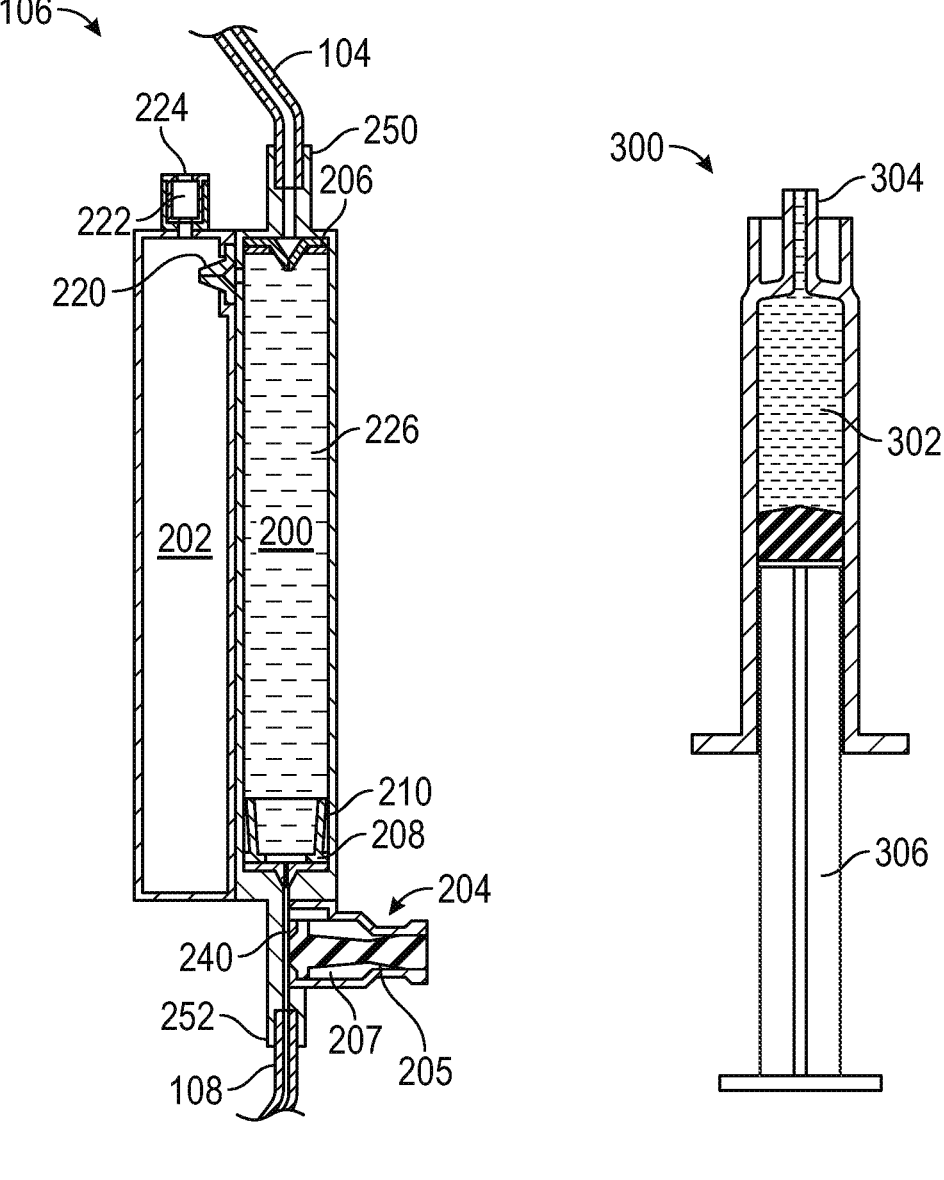
FIG. 2                    FIG. 3

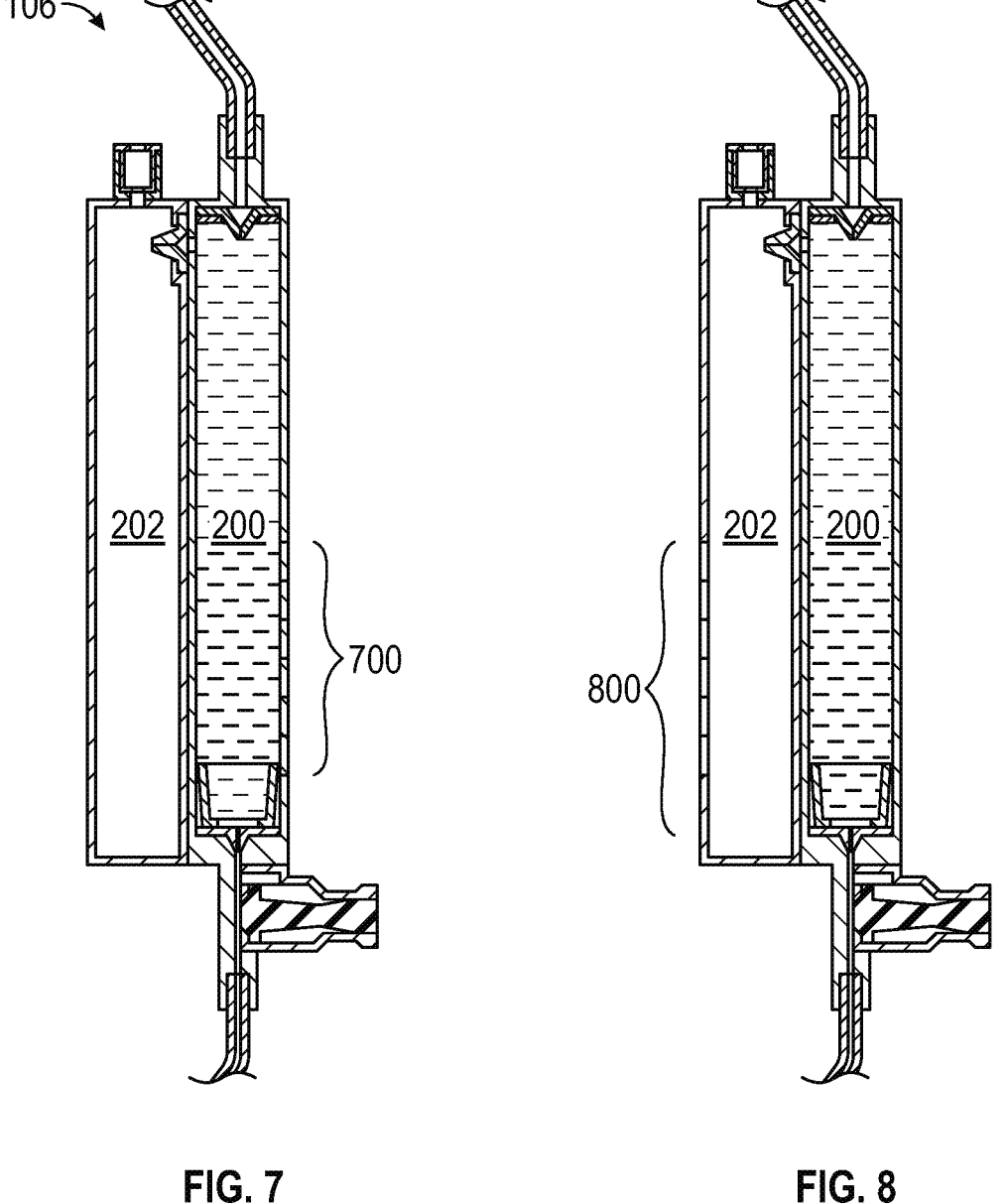
FIG. 7                              FIG. 8

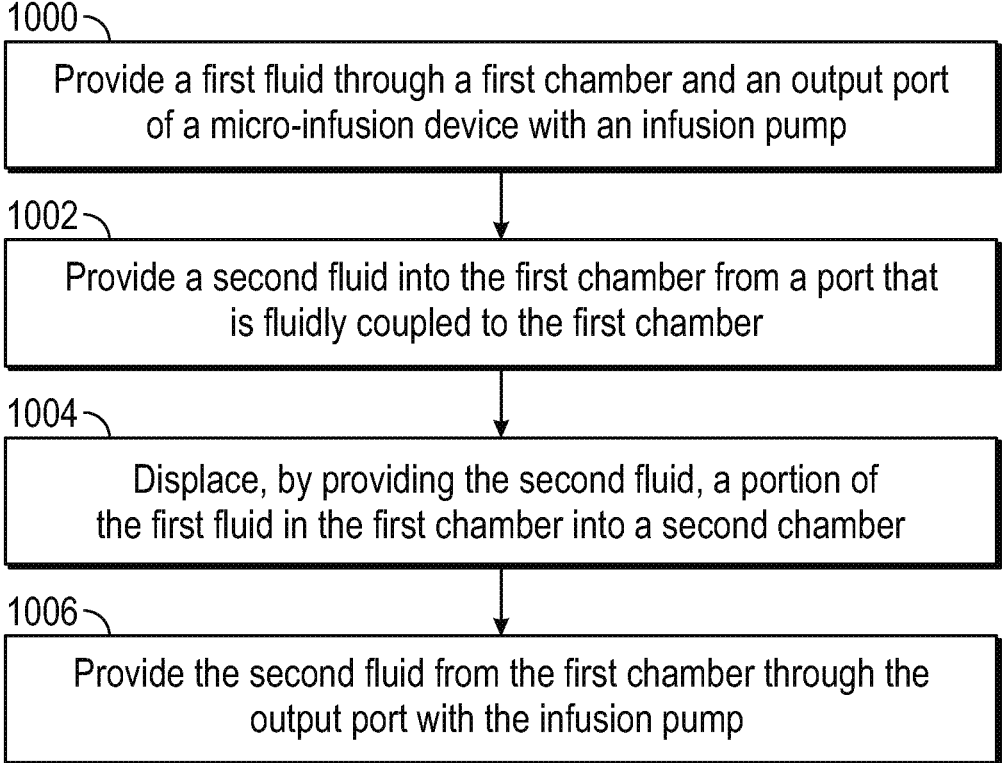

1000 ⌐
Provide a first fluid through a first chamber and an output port
of a micro-infusion device with an infusion pump 1002 ⌐
Provide a second fluid into the first chamber from a port that
is fluidly coupled to the first chamber 1004 ⌐
Displace, by providing the second fluid, a portion of
the first fluid in the first chamber into a second chamber 1006 ⌐
Provide the second fluid from the first chamber through the
output port with the infusion pump

FIG. 10

MICRO-INFUSION DEVICE AND INFUSION SET

CROSS-REFERENCE TO RELATED APPLICATIONS

This application is a continuation patent application of divisional patent application Ser. No. 16/393,749, filed on Apr. 24, 2019, entitled "MICRO-INFUSION DEVICE AND INFUSION SET," now U.S. Pat. No. 11,103,635, which issued on Aug. 31, 2021, which is a divisional of patent application Ser. No. 15/414,556, filed on Jan. 24, 2017, entitled "MICRO-INFUSION DEVICE AND INFUSION SET," now U.S. Pat. No. 10,314,966, which issued on Jun. 11, 2019, which claims the benefit of priority under 35 U.S.C. § 119 as a nonprovisional of U.S. Provisional Patent Application Ser. No. 62/287,840, filed on Jan. 27, 2016, entitled "MICRO-INFUSION DEVICE AND INFUSION SET," the disclosures of which are hereby incorporated by reference in their entirety for all purposes.

TECHNICAL FIELD

The present disclosure generally relates to the administration of medical fluid by infusion and, in particular, relates to systems and methods for providing and pumping medical fluid.

BACKGROUND

Infusion pumps have become commonplace within the healthcare industry as devices for precisely administering intravenous (IV) fluids. Use of a pump in place of an elevated fluid container with a simple roller clamp to control the flow of the IV fluid allows more accurate and consistent control of the rate of delivery of the fluid to the patient.

The assembly of tubing, valves, fittings, and needles that connect the fluid container to the patient may be referred to as an "IV set." IV sets are typically disposable to reduce the risk of infection and contamination. In some infusion pump/IV set systems, a drug for delivery to the patient is provided at or above the pump. In these systems, a fluid such as saline that fills the tubing between the pump and the patient is thus provided to the patient before any of the drug reaches the patient. In some systems, a milliliter or more of fluid can be disposed in the tube which, pumping at one milliliter per hour, can cause a delay of up to one hour before the drug reaches the patient. These systems can be undesirable in some situations if care is not taken.

SUMMARY

One or more embodiments including a method including receiving, with an infusion pump, a set identifier that identifies a micro-infusion device, determining at least one property associated with the micro-infusion device based on the received set identifier, and operating the infusion pump, at least in part, based the determined at least one property to provide a first fluid and a second fluid through a first chamber and an output port of the micro-infusion device, wherein a portion of the first fluid in the first chamber is displaced into a second chamber of the micro-infusion device after the second fluid is received into the first chamber from a port coupled to the first chamber.

One or more embodiments including a non-transitory computer-readable medium having instructions executable by at least one processor to cause an infusion pump to receive a set identifier that identifies a micro-infusion device, determine at least one property associated with the micro-infusion device based on the received set identifier, and provide, based on the determined at least one property, a first fluid and a second fluid through a first chamber and an output port of the micro-infusion device, wherein a portion of the first fluid in the first chamber is displaced into a second chamber of the micro-infusion device after the second fluid is received into the first chamber from a port coupled to the first chamber.

Aspects of the subject technology relate to the micro-infusion of medical fluids using a micro-infusion device. The micro-infusion device may include one or more chambers, one or more fixed valves, and one or more sliding valves and may be disposed in an intravenous (IV) set between an infusion pump and a patient. As described in greater detail hereinafter, the valves and chambers of the micro-infusion device may be arranged and configured to facilitate infusion of a medical fluid to a patient without the need to provide large volumes of saline or other solutions to the patient.

In accordance with certain aspects, a micro-infusion device is provided that includes a first chamber having an input port and an output port. The micro-infusion device also includes a first valve disposed between the input port and the first chamber. The micro-infusion device also includes a second valve disposed on a moveable piston that is moveable within the first chamber. The micro-infusion device also includes a second chamber disposed adjacent the first chamber. The micro-infusion device also includes a third valve disposed between the first chamber and the second chamber. The micro-infusion device also includes a needle-free port configured to be fluidly coupled to the first chamber.

In accordance with certain aspects, an intravenous (IV) set is provided that includes first tubing configured to be coupled to a fluid source. The IV set also includes a micro-infusion device having an input port coupled to the first tubing. The micro-infusion device also includes a first chamber having an input port and an output port, a first valve disposed between the input port and the first chamber, a second valve disposed on a moveable piston that is moveable within the first chamber, a second chamber disposed adjacent the first chamber, a third valve disposed between the first chamber and the second chamber, a needle-free port having a port chamber that is fluidly coupled to the first chamber, and an output port. The IV set also includes second tubing coupled to the output port.

In accordance with certain aspects, a method is provided that includes providing a first fluid through a first chamber and an output port of a micro-infusion device with an infusion pump. The method also includes providing a second fluid into the first chamber from a port that is fluidly coupled to the first chamber. The method also includes displacing, by providing the second fluid, a portion of the first fluid in the first chamber into a second chamber. The method also includes providing the second fluid from the first chamber through the output port with the infusion pump.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 2 illustrates a cross-sectional side view of a micro-infusion device according to certain aspects of the present disclosure.

FIG. 3 illustrates cross-sectional side view of a syringe according to certain aspects of the present disclosure.

FIG. 7 illustrates a cross-sectional side view of a micro-infusion device according to certain aspects of the present disclosure.

FIG. 8 illustrates a cross-sectional side view of a micro-infusion device according to certain aspects of the present disclosure.

FIG. 10 illustrates a flow diagram of an example process for micro-infusion in accordance with various aspects of the subject technology.

DETAILED DESCRIPTION

Figure 1:
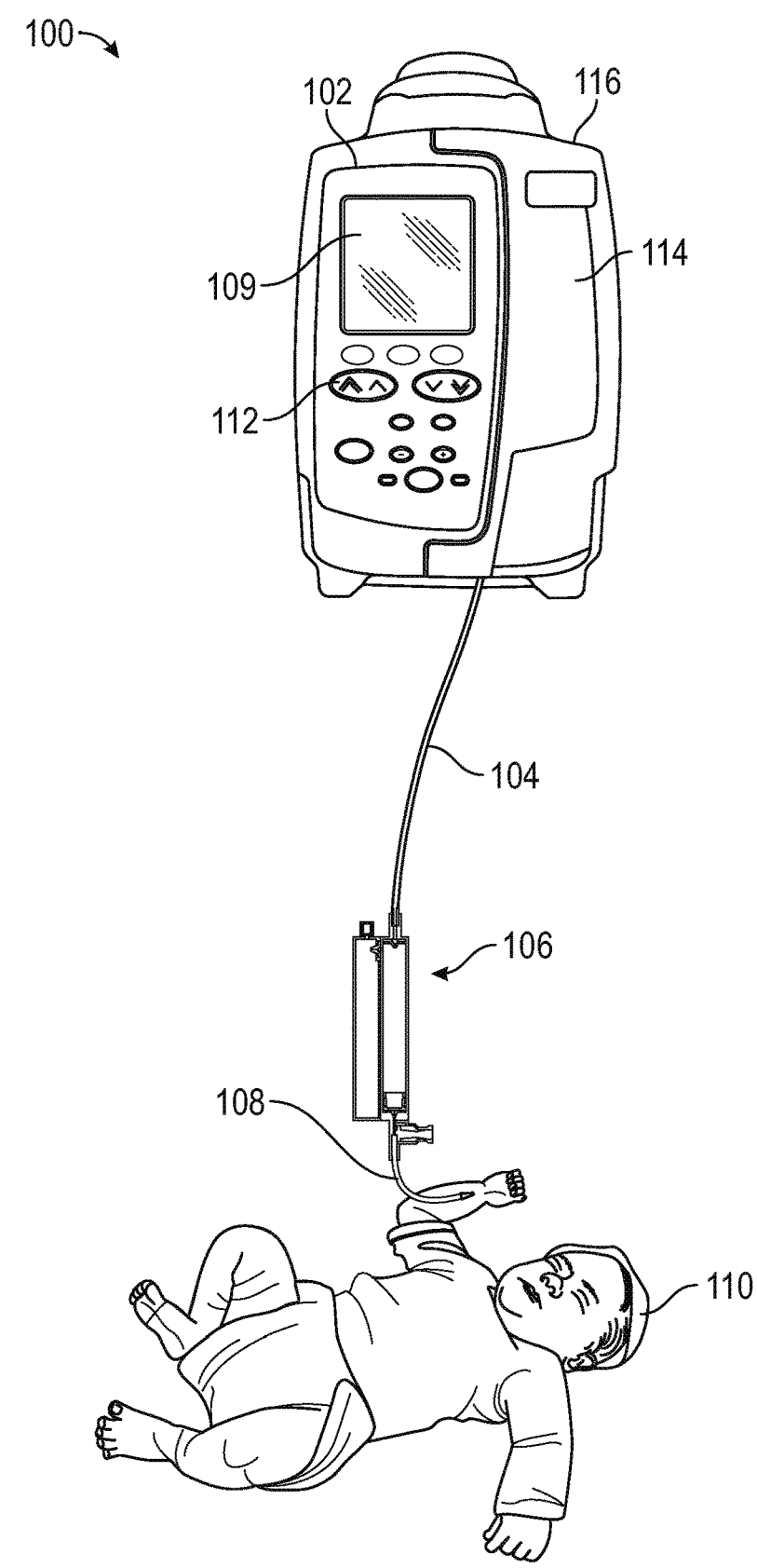
FIG. 1 is a diagram of a system for administering medical fluid to a patient using an IV pump and a micro-infusion device according to certain aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

According to various embodiments, a micro-infusion device is provided. The micro-infusion device may be provided at a location along an infusion line between an infusion pump and a patient. The micro-infusion device may facilitate delivery of a volume of drug dose to the patient (e.g., a baby such as a prematurely-born baby), without large volumes for priming or flushing the infusion line. The micro-infusion device may be used to deliver the drug dose into the infusion line at a location that is close to the patient to reduce time to delivery initiation, while still allowing the delivery rate to be controlled by the pump and allowing a seamless return to, for example, saline delivery (or delivery of any other administered drug compatible with the micro-infusion solution, such as D5W) upon completion of the dose delivery. The micro-infusion device may also provide the additional benefit of allowing observing of the progress of the dose delivery in some embodiments. The micro-infusion device may be configured to facilitate delivery of target volumes of between, for example, 0.5 cc and 5 cc at flow rates between 0.05 cc/hr or 0.1 cc/hr and 10 cc/hr (as examples). Further details of the micro-infusion device are provided hereinafter.

While the following discussion is directed to the administration of medical fluid to a patient by a caregiver using an IV pump, the disclosed methods and configurations may be used for other medical and non-medical applications and may be used by other individuals (e.g., a patient self-administering a medical fluid at home).

FIG. 1 is a diagram of a system 100 for administering medical fluid to a patient. As shown, an infusion system 100 such as a neonatal infusion system may include an infusion pump 102 that controls delivery of a medical fluid to a patient 110 via tubing fluidly coupled between the pump 102 and the patient 110. In the example of FIG. 1, patient 110 is a neonate such as a prematurely-born baby or preemie.

Infusion system 100 may include a multi-chambered device such as micro-infusion device 106 that is integrated with the tubing that runs between pump 102 and patient 110. Micro-infusion device 106 may be used to provide intermittent infusions of small doses of a medication to a patient such as an infant. In the example of FIG. 1, tubing 104 fluidly couples micro-infusion device 106 with pump 102 and tubing 108 fluidly couples micro-infusion device 106 to patient 110. Tubing 104 may be substantially longer than tubing 108 so that a medical fluid such as a liquid drug for patient 110 can be introduced into the tubing at a location close to the patient. In this way, a drug dose may be introduced into the infusion line via micro-infusion device 106 at a location that is close to the patient to reduce time to delivery initiation.

A fluid such as saline or other medical fluids may be provided from pump 102 to tubing 104 in a controlled matter. As shown, pump 102 may include a display 109, control features 112 and pump mechanism 114. Fluids to be pumped into tubing 104 may be provided from a fluid source located at the pump mechanism (e.g., a syringe or vial loaded into the pump mechanism) or via a fluid container (e.g., an IV bag) disposed above the pump and fluidly coupled through the pump via an input 116 (e.g., via a length of tubing and/or a pump cassette attached to tubing that is attached to the fluid container). Tubing of the IV set may interface with pump 102 via a length of tubing that is captured and manipulated by pump 102 or the IV set may include a pump cassette integrated with the tubing (superior to the microinfusion device) that is configured to be received in a cassette recess of the pump and that includes various valves, pistons, and/or other controllable components configured to be operated by pump 102 to move fluids through the IV set. In configurations in which the IV set includes a pump cassette, the pump cassette may include a coded identifier (e.g., a bar code) or an RFID tag that identifies the set (e.g., including identifying aspects such as chamber volumes and/or valve cracking pressures of the microinfusion device).

FIG. 2 shows an enlarged cross-sectional side view of micro-infusion device 106. As shown in FIG. 2, micro-infusion device 106 may be a multi-chambered device having a first chamber 200 and a second chamber 202. Tubing 104 may be coupled to first chamber 200 by an input valve 206 disposed between an input port 250 of chamber 200 and chamber 200 itself. Input valve 206 may be a check valve that allows fluid 226 (e.g., saline) to flow from tubing 104 into chamber 200, if the cracking pressure of valve 206 is reached, and that prevents flow of fluid from chamber 200 into tubing 104.

A second valve such as sliding output valve 208 may also be provided in chamber 200. As shown, sliding output valve 208 may be attached to a moveable piston 210 that is configured to move within chamber 200 responsive to various fluid pressures on valve 208. Sliding output valve 208 may be, for example, a check valve that allows fluid 226 to flow through the valve from chamber 200 to tubing 108 if the cracking pressure of the valve 208 is reached when the piston 210 and valve 208 are located at the bottom of chamber 200 as in the configuration of FIG. 2. Tubing 108 may be coupled to chamber 200 at an output port 252.

An input port 204 such as a needle-free valve may also be coupled to chamber 200 via fluid pathway 240. Needle-free valve 204 may, for example, be a SmartSite® needle-free valve as provided by Becton, Dickinson and Company. As shown in FIG. 2, needle-free valve 204 may include a compressible valve member 205 (e.g., a silicone valve member) disposed in a chamber 207. As discussed in further detail hereinafter, a medical fluid such as a liquid drug can be introduced into chamber 200 via needle-free port 204 for delivery to the patient. Piston displacement of liquid in chamber 200 (e.g., by movement of piston 210 and valve 208) occurs when fluid is introduced through needle-free valve 204, with direct flow through piston 210 impeded by valve 208.

In various embodiments, tubing 104 and 108 and device 106 may be primed prior to coupling of tubing 108 to the patient. Priming the system may include using a syringe above device 106 to generate sufficient pressure to crack valves 206 and 208 to allow fluid to flow into chamber 200 and tubing 108 and/or utilizing a defeat mechanism (not explicitly shown) on valve 208 to allow the fluid to flow into chamber 200 and tubing 108.

Device 106 may include an additional valve 220 disposed between chamber 200 and chamber 202 that allows fluid 226 to flow from chamber 200 into chamber 202 when the cracking pressure of valve 220 (e.g., a check valve) is reached. Valve 220 also prevents flow of fluid from chamber 202 into chamber 200. In this way, chamber 202 may be configured as an overflow chamber or dump chamber so that fluid such as fluid 226 can be dumped from chamber 200 into chamber 202. As shown, valve 220 may be disposed at the at an end (e.g., a top end or a pump-side end of a wall that separates chambers 200 and 202) that is distal to the end at which port 204 and fluid pathway 240 are formed (e.g., a bottom end or a patient-side end). With this configuration of chambers 200 and 202 and valve 220, only fluid located at the top (pump side) of the chamber 200 can be pushed through valve 220 into chamber 202. With this configuration of chambers 200 and 202 and valve 220, the full volume of chamber 200 can be passed into the dump chamber 202 as the microinfuser is charged with a drug from port 204 or line 108. In the configuration shown in FIG. 2, piston-mounted valve 208 is prevented, by piston 210 from moving past (e.g., above) valve 220. With this configuration of chambers 200 and 202 and valves 208 and 220, only fluid located above valve 208 and piston 210 (e.g., fluid 226) can pass through valve 220, and fluid introduced into chamber 200 from port 204 or line 108 may be prevented from passing through valve 220 into chamber 202 by piston-mounted valve 208.

A vent such as vent 222 may be provided at the top (e.g., pump side) of chamber 202 that allows air in chamber 202 to escape to the external environment if displaced by fluid 226 flowing into chamber 202 from chamber 200. A filter 224 may be provided in the vent 222 to prevent contaminants from flowing into or out of chamber 202 and to prevent dump liquid from being ejected from the chamber while permitting air to exit. Exit of air through vent 222 prevents a pressure build up in the dump chamber. Filter 224 may be, for example, a sterilizing quality filter such as a 0.2 micron filter, a check valve, and/or a hydrophobic/hydrophilic membrane or the like that prevents loss of fluid from chamber 202 while allowing air to exit from chamber 202. A 0.2 micron filter may be used to prevent microbial contamination of the environment by the exiting air. A medical fluid such as a liquid drug to be administered to the patient may be provided into chamber 200 via a source such as a syringe that is attached to port 204. FIG. 3 shows a cross-sectional view of an example of a needle-free syringe 300 filled (e.g., at a pharmacy or by a caregiver) with a medical fluid 302 (e.g., a liquid drug). A plunger 306 may be configured to be compressed to provide fluid 302 through a needle-free output port 304 of the syringe.

Referring again to FIG. 2, in various embodiments, chambers 200 and 202 may each be configured to hold between, for example, 10 cc and 20 cc of fluid. Chambers 200 and 202 may have a common volume or may have different volumes. Chamber 202 may have a volume determined by the number of doses the micro-infusion device is expected to be used for. For example, device 106 may be configured to be used for infusion of two doses of a medication without being replaced. In this example, chamber 202 may have a volume of approximately 2.5 times the volume of the expected dose, so that a volume of fluid 226 equal to the volume two of doses of the liquid drug can be stored within chamber 202. The example of two doses is merely illustrative. In some embodiments, the number of doses may be chosen based on a frequency of the intended infusion and the length of a nursing shift, so that a single IV set with a single micro-infusion device can be used throughout a nursing shift.

The cracking pressures of valves 206, 208, and 220 may configured so that valve 206 has the lowest cracking pressure, valve 220 has the highest cracking pressure, and valve 208 has a cracking pressure between the cracking pressure of valves 206 and 220 for proper control of fluids through device 106. As examples, valve 206 may have a cracking pressure of less than 2 psi, valve 208 may have a cracking pressure of between 5 psi and 10 psi, and valve 220 may have a cracking pressure equal to or above the maximum pump pressure of the pump (e.g., equal to or above approximately 20 psi). In this way, the pump can provide pressure to move fluid 226 through valves 206 and 208 without cracking valve 220. Valve 220 may be configured to crack in response to pressure generated by a syringe attached to port 204. Valve 208 may have a cracking pressure that is greater than the pressure required to slide piston 210 (to which valve 208 is attached) within chamber 200. In this way, valve 208 may be configured to be moved to the bottom of chamber 200 (as in the configuration of FIG. 2) by fluid 226 before valve 208 is cracked. However, the above examples in which the cracking pressure of valve 206 is less that the cracking pressure of valve 208 are merely illustrative. In these examples, the cracking pressure of the valve 206 is low to prevent occlusion alarms. However, in some embodiments, valve 206 may have a cracking pressure equal to or greater than the cracking pressure of valve 208 and less than the cracking pressure of valve 220.

The IV set that includes device 106 may have a set ID that can be scanned or otherwise provided to pump 102. Upon set recognition by the pump based on the set ID, pump 102 may reconfigure the maximum pump pressure to allow a reasonable cracking pressure of valve 220, to facilitate filling the chamber 200 (e.g., to reduce the syringe force necessary to displace piston 210). Moreover, medication errors can be reduced due to the combination of a set ID and microinfusion technology disclosed herein. For example, with a set ID (e.g., a cassette barcode or RFID), the pump 102 may identify a microinfusion set which is associated with a specific dosed medication and tubing chamber volumes and can monitor line pressures and/or infused volumes to ensure proper delivery of the expected dose.

FIGS. 4A, 4B, 4C, and 4D show cross-sectional side views of micro-infusion device 106 in various stages of operation during infusion of a medical fluid to a patient.

Figures 4A, 4B:
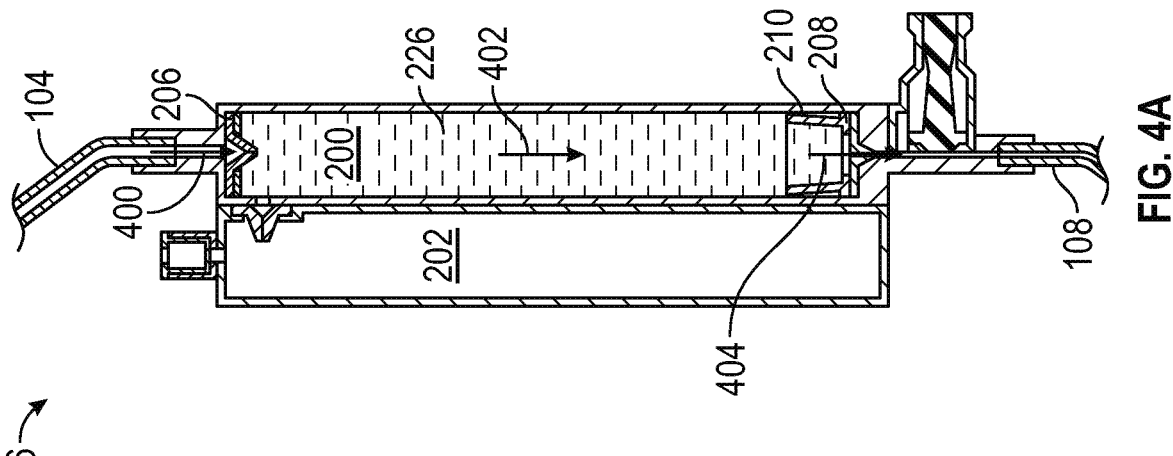
FIGS. 4A-4D illustrate cross-sectional side views of a micro-infusion device in various configurations according to certain aspects of the present disclosure.

In the configuration of FIG. 4A, fluid 226 is flowing from tubing 104, through valve 206 (as indicated by arrow 400), through chamber 200 (as indicated by arrow 402), and through valve 208 (as indicated by arrow 404) into output tubing 108 (e.g., to the patient) under control of pump 102 (see FIG. 1).

In the configuration of FIG. 4B, syringe 300 has been attached to needle-free valve 204, plunger 306 is being compressed (as indicated by arrow 412), and medical fluid 302 is being pushed into chamber 200 (as indicated by arrow 410). In this configuration, chamber 200 may have a proximal (e.g., pump-side) portion 450 behind/above piston 210 and a distal (e.g., patient-side) portion 452 in front of (below) piston 210. The distal portion 452 (when piston 210 is displaced from the full forward position) contains the microinfuser drug 302, while proximal portion 450 behind the piston contains the IV fluid 226 only. Pressure generated by the flow of fluid 302 into chamber 200 has pushed piston 210 and valve 208 upward in the direction of valve 206. Because valve 206 prevents any flow backward into tubing 104 a portion 226D of fluid 226 flows through valve 220 into chamber 202 (as indicated by arrow 414). Fluid 226D may displace air in chamber 202 such that the air is vented to the external environment through vent 222 (as indicated by arrow 416). As shown in FIG. 4B, compressible member 205 may be compressed by syringe 300 so as to prevent flow of fluid 302 directly from the syringe to the patient. In this way, fluid 302 can be provided into chamber 200. However, in other embodiments, compressible member 205 may be replaced with by other components such as a mechanism or another type of valve that prevents flow of fluid 302 directly from the syringe to the patient and allows fluid flow into chamber 200. Piston 210 and valve 208 separate drug 302 from fluid 226. Piston 210 (sometimes referred to as a plunger) may be configured so that, if piston 210 is pushed all the way to the top (pump side) of chamber 200, plunger 210 blocks access to valve 220 so that drug 302 is prevented from flowing into chamber 202. In this way, dilution of drug 302 and/or inaccurate dose delivery can be prevented.

Figures 4C, 4D:
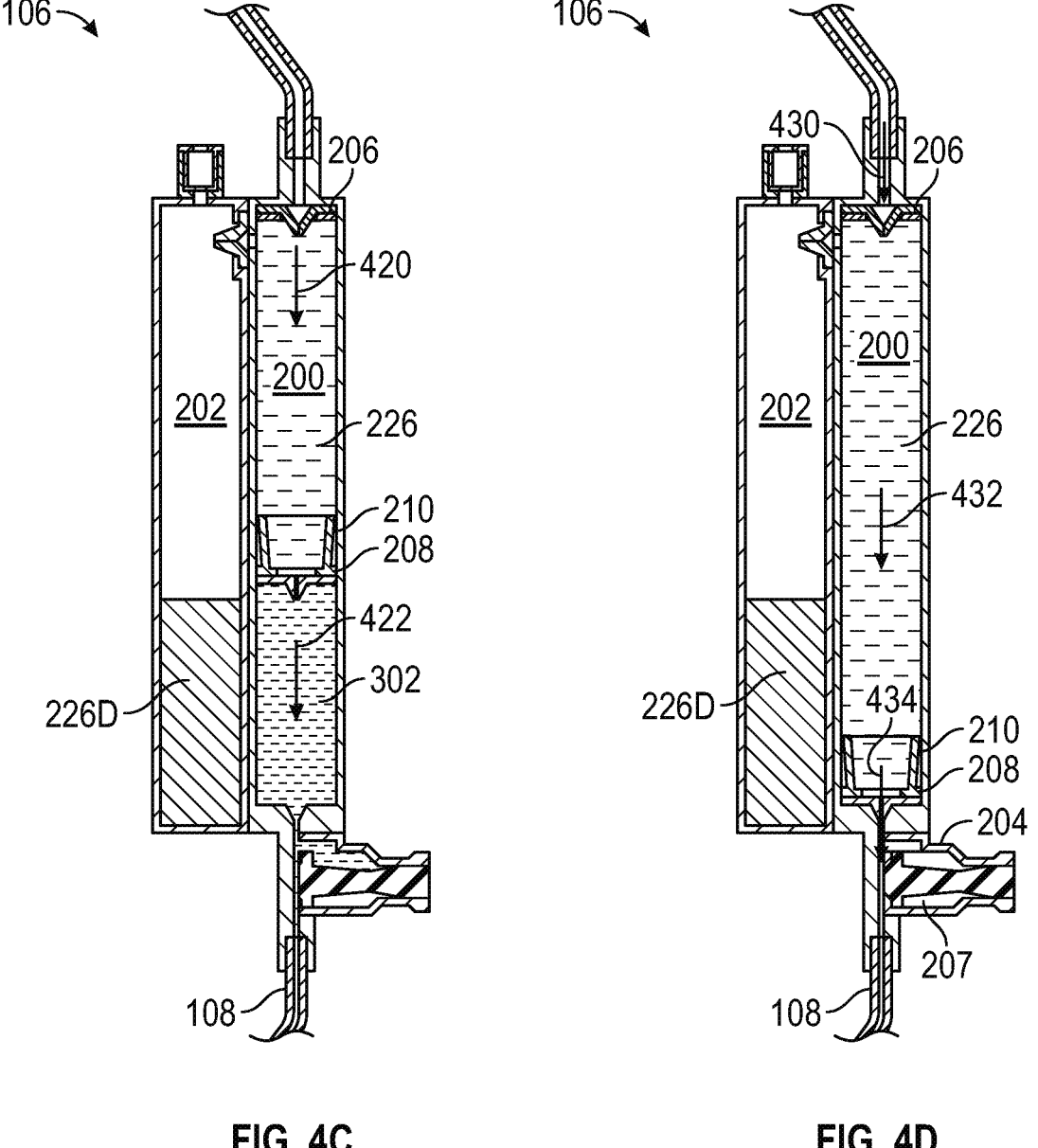

In the configuration of FIG. 4C, syringe 300 has been removed from valve 204, leaving fluid 302 in chamber 200. In this configuration, pump 102 continues pumping fluid 226 into chamber 200 through valve 206 (as indicated by arrow 420) causing fluid 226 to push piston 210 and valve 208 downward toward tubing 108. This downward pressure on piston 210 and valve 208 moves piston 210 and valve 208 downward, thereby pushing medical fluid 302 out of chamber 200 and into tubing 108 (as indicated by arrow 422) (e.g., to be delivered to the patient) under control of pump 102.

In the configuration of FIG. 4D, all of the medical fluid 302 has been pushed from chamber 200 (e.g., and delivered to the patient) and fluid 226 seamlessly follows fluid 302 from chamber 200 when piston 210 and valve 208 reach the bottom of chamber 200 to resume providing fluid 226 through device 106 (e.g., to the patient). In this configuration, fluid 226 is again flowing through valve 206 (as indicated by arrow 430), through chamber 200 (as indicated by arrow 432), and through valve 208 (as indicated by arrow 434) into output tubing 108 (e.g., to the patient) under control of pump 102 while the dumped portion 226D of fluid 226 remains within chamber 202. As shown in FIG. 4D, the amount of fluid 226D dumped into chamber 202 may be less than half the volume of the chamber so that an additional dose can be provided in the same manner described above in connection with FIGS. 4A-4C without replacing the IV set or micro-infusion device 106. Because the amount of fluid 226D in chamber 202 is equal to the amount of drug pushed into chamber 200 and provided to the patient, the amount of drug provided and/or the number of doses provided can be measured by viewing the amount of fluid 226D in chamber 202 and/or by viewing a witness line or "fiducial line" formed by the front of the stopper/plunger 210.

As shown in FIG. 4D, chamber 207 may be fluidly coupled to chamber 200 so that fluid 226 automatically flushes chamber 200, chamber 207, and tubing 108 when fluid 226 is pushed through device 106 following administration of fluid 302 to the patient.

Figure 5:
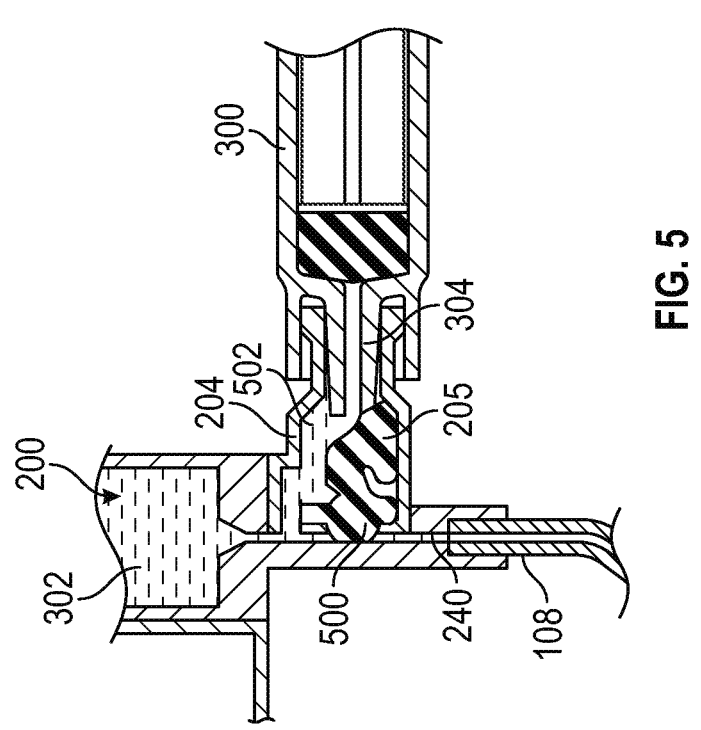
FIG. 5 illustrates an enlarged cross-sectional side view of a portion of the micro-infusion device of FIG. 4B according to certain aspects of the present disclosure.

FIG. 5 is an enlarged cross sectional view of a portion of micro-infusion device 106 in the configuration of FIG. 4B with syringe 300 attached to port 204. As shown in FIG. 5, when syringe 300 is attached to port 204, output port 304 of syringe 300 compresses compressible member 205 such that a pathway 502 is opened for fluid 302 to flow from syringe 300 into chamber 200 and such that a forward portion 500 of compressible member 205 extends into pathway 240 to close pathway 240, thereby blocking fluid 302 from being provided directly to the patient from syringe 300 and separating fluid 302 from being diluted by fluid 226.

Figure 6:
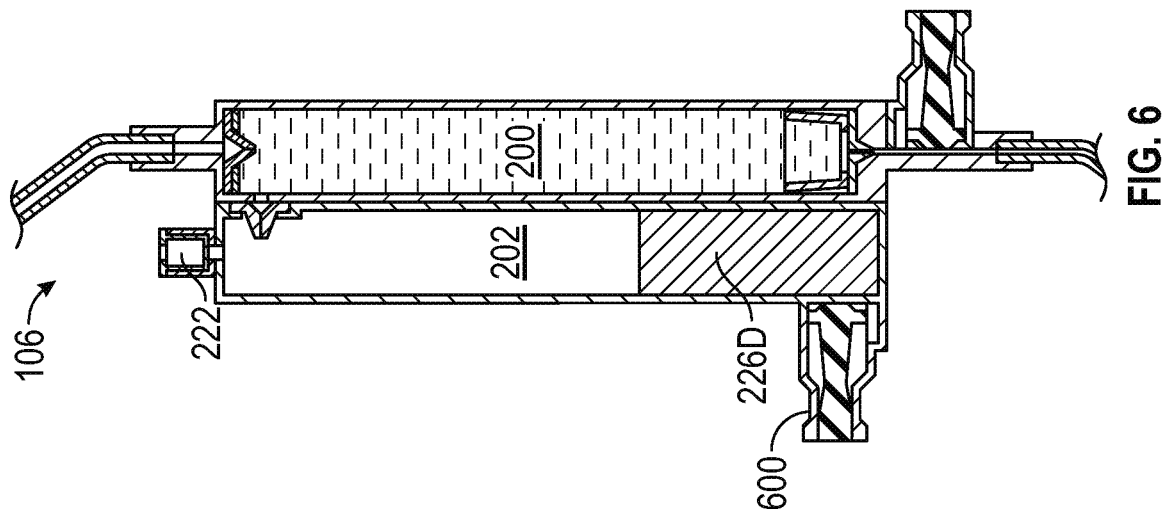
FIG. 6 illustrates a cross-sectional side view of a micro-infusion device with an output port in a dump chamber according to certain aspects of the present disclosure.

In the embodiments described above, fluid 226D that is dumped from chamber 200 into chamber 202 when medical fluid 302 is introduced into chamber 202 is merely stored within chamber 202 until the IV set, including device 106 is removed and replaced. However, this is merely illustrative. As shown in FIG. 6, in some embodiments, chamber 202 may be provided with an output port 600 such as another needle-free valve (e.g., a SmartSite® valve or an open Luer port with a cap) through which a caretaker such as a nurse can remove fluid 226 from chamber 202 (e.g., by connecting a needle-free syringe to port 600). In this embodiment, when fluid 226D is removed from chamber 202, air may flow into chamber 202 via vent 222. The low resistance to air flow of filter 224 compared to the high cracking pressure of valve 220 prevents fluid from being pulled from chamber 200.

In various other embodiments, chamber 202, separated from chamber 200 by valve 220, may be implemented as a remote chamber that is fluidically connected to chamber 200 by tubing. In these embodiments, a benefit may be provided that the second (overflow) chamber could be much larger than the first chamber 200 (e.g., to hold the overflow from many doses). Moreover, providing a remote chamber may help remove a large volume away from the patient's immediate space. In yet another embodiment, chamber 202, separated from chamber 200 by valve 220, may be replaced by a syringe coupled to chamber 200.

As noted above, it can be desirable to be able to observe the progress of the dose delivery during delivery of the dose. As shown in FIG. 7, chamber 200 may be provided with graduated markings 700 so that a caretaker can directly measure how much of drug 302 has been provided into chamber 200 and monitor how much of the drug has subsequently been delivered to the patient at any time (e.g., by observing the plunger fiducial line on or relative to the graduated markings).

As shown in FIG. 8, in another embodiment, chamber 202 may have graduated markings 800 so that the amount of drug 302 that has been introduced into chamber 200 can be indirectly measured by observing the amount of fluid 226D in chamber 202. In this way, a record of the amount of drug 302 that has been provided can be stored by the fluid 226D in chamber 202 as the amount of fluid 226D in chamber 202 will not change as fluid 302 is delivered to the patient or after delivery of fluid 302. In other embodiments, both chambers 200 and 202 may be provided with graduated markings so that real time observation (e.g., using markings 700) of the amount of drug 302 being delivered and a historical record (e.g., using markings 800) of the amount of drug 302 infused can be provided.

Figure 9:
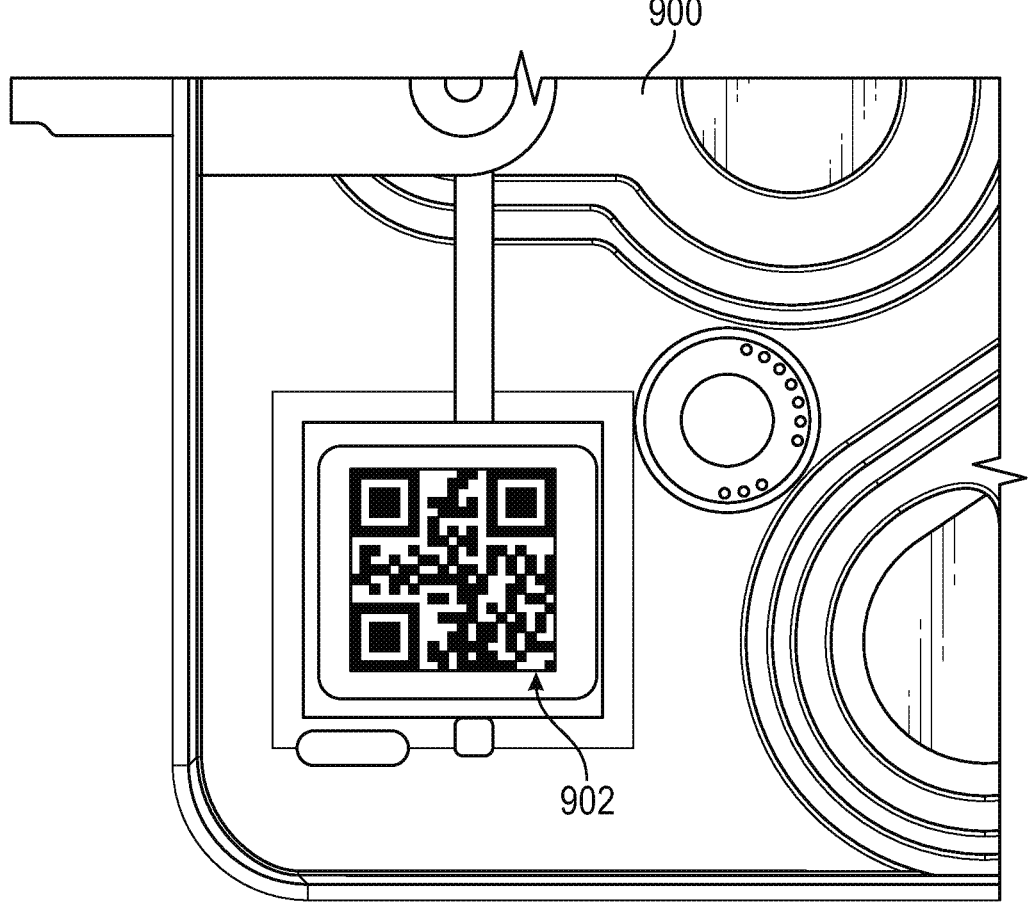
FIG. 9 illustrates top view of a portion of a pump cassette according to certain aspects of the present disclosure.

Device 106 may be provided as an integral part of an IV set (e.g., an IV set including tubing 104 and 108, a fluid container connected to tubing 104, and/or a catheter assembly). The IV set may include a cartridge coupled to tubing 104, the cartridge configured to be installed in pump 102 and manipulated thereby to pump fluid into tubing 104. As shown in FIG. 9, a cartridge 900 may have an identifier 902 (e.g., a bar code or other coded identifier, or radio frequency identification (RFID) including a set identifier (ID) and/or a set type) that identifies to the components of the IV set, including the micro-infusion device. In this way, pump 102 may be provided with the characteristics of the micro-infusion device and may be able to set operating limits and configure sensors to detect any operational problems in the IV set, including in the micro-infusion device. Examples of operational limits and the use thereof based on characteristics of a medical device coupled to an infusion pump can be found, for example, in U.S. Pat. No. 8,038,593 which is hereby incorporated by reference herein in its entirety.

FIG. 10 depicts a flow diagram of an example process for micro-infusion, according to aspects of the subject technology. For explanatory purposes, the example process of FIG. 10 is described herein with reference to the components of FIG. 1-FIG. 9. Further for explanatory purposes, the blocks of the example process of FIG. 10 are described herein as occurring in series, or linearly. However, multiple blocks of the example process of FIG. 10 may occur in parallel. In addition, the blocks of the example process of FIG. 10 need not be performed in the order shown and/or one or more of the blocks of the example process of FIG. 10 need not be performed.

In the depicted example flow diagram, at block 1000, a first fluid (e.g., a saline solution such as fluid 226 as described herein) may be provided through a first chamber such as chamber 200 and an output port such as output port 252 of a micro-infusion device such as micro-infusion device 106 with an infusion pump such as infusion pump 102. For example, the first fluid may be provided through the output port to a patient (e.g., via tubing such as tubing 108 coupled to the output port and a catheter at the patient). Providing the first fluid through the first chamber of the micro-infusion device with the infusion pump may include providing the first fluid through a first valve such as valve 206 into the first chamber and providing the first fluid out of the first chamber through a second valve such as valve 208 that is disposed on a moveable piston such as moveable piston 210.

At block 1002, a second fluid such as a liquid drug (e.g., fluid 302 as described herein) may be provided into the first chamber from a port such as port 204 that is fluidly coupled to the first chamber. Providing the second fluid into the first chamber from the port that is fluidly coupled to the first chamber may include compressing a compressible member of the port to open a fluid pathway between a syringe and the first chamber and to close a fluid pathway between the first chamber and the output port.

At block 1004, at least a portion of the first fluid in the first chamber may be displaced into a second chamber (e.g., chamber 202) by providing the second fluid. Air in the second chamber may be displaced through a vent such as vent 222 in the second chamber with the portion of the first fluid. Displacing, by providing the second fluid, a portion of the first fluid in the first chamber into the second chamber may include pushing, with the second fluid, the moveable piston and the second valve toward the first valve. Displacing, by providing the second fluid, a portion of the first fluid in the first chamber into the second chamber may also include pushing, with the moveable piston and the second valve, the portion of the first fluid through a third valve such as valve 220 disposed between the first chamber and the second chamber.

At block 1006, the second fluid may be provided from the first chamber through the output port with the infusion pump. Following the provision of the second fluid, additional first fluid may be provided through the first chamber and the output port while the portion of the first fluid remains in the second chamber. In some scenarios, the portion of the first fluid may be removed from the second chamber via a port such as port 600 in the second chamber.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A micro-infusion device, comprising:
  a first chamber having an input port and an output port;
  a first valve disposed between the input port and the first chamber;
  a second valve disposed on a moveable piston that is moveable within the first chamber;

a second chamber disposed adjacent the first chamber;

a third valve disposed between the first chamber and the second chamber; and a needle-free port configured to be fluidly coupled to the first chamber.

Concept 2. The micro-infusion device of Concept 1 or any other Concept, wherein the first valve, the second valve, and the third valve are each check valves.

Concept 3. The micro-infusion device of Concept 2 or any other Concept, wherein the first valve has a first cracking pressure, wherein the second valve has a second cracking pressure, wherein the third valve has a third cracking pressure, wherein the first cracking pressure is less than the second cracking pressure, and wherein the second cracking pressure is less than the third cracking pressure.

Concept 4. The micro-infusion device of Concept 1 or any other Concept, further comprising a vent coupled between the second chamber and an external environment.

Concept 5. The micro-infusion device of Concept 4 or any other Concept, wherein the vent comprises a filter or a check valve.

Concept 6. The micro-infusion device of Concept 4 or any other Concept, wherein the input port is configured to receive a first fluid from first tubing coupled to the input port.

Concept 7. The micro-infusion device of Concept 6 or any other Concept, wherein the moveable piston is configured to be moved toward the first valve by a second fluid introduced at the needle-free port and to push a portion of the first fluid through the third valve into the second chamber.

Concept 8. An intravenous (IV) set, comprising:

first tubing configured to be coupled to a fluid source;

a micro-infusion device having an input port coupled to the first tubing, the micro-infusion device further comprising:

a first chamber having an input port and an output port, a first valve disposed between the input port and the first chamber, a second valve disposed on a moveable piston within the first chamber, a second chamber disposed adjacent the first chamber, a third valve disposed between the first chamber and the second chamber, a needle-free port having a port chamber that is fluidly coupled to the first chamber, and an output port; and second tubing coupled to the output port.

Concept 9. The IV set of Concept 8 or any other Concept, further comprising a pump cassette coupled to the first tubing, the pump cassette configured to interface with an infusion pump and having a set identifier.

Concept 10. The IV set of Concept 8 or any other Concept, further comprising a fluid container fluidly coupled to the first tubing.

Concept 11. The IV set of Concept 10 or any other Concept, further comprising a catheter assembly coupled to the second tubing.

Concept 12. The IV set of Concept 11 or any other Concept, wherein the first tubing is longer than the second tubing.

Concept 13. A method, comprising:

providing a first fluid through a first chamber and an output port of a micro-infusion device with an infusion pump;

providing a second fluid into the first chamber from a port that is fluidly coupled to the first chamber;

displacing, by providing the second fluid, a portion of the first fluid in the first chamber into a second chamber; and providing the second fluid from the first chamber through the output port with the infusion pump.

Concept 14. The method of Concept 13 or any other Concept, further comprising, displacing air in the second chamber through a vent in the second chamber with the portion of the first fluid.

Concept 15. The method of Concept 14 or any other Concept, further comprising, following the providing of the second fluid, providing additional first fluid through the first chamber and the output port while the portion of the first fluid remains in the second chamber.

Concept 16. The method of Concept 15 or any other Concept, further comprising removing the portion of the first fluid from the second chamber via a port in the second chamber.

Concept 17. The method of Concept 13 or any other Concept, wherein providing the first fluid through the first chamber of the micro-infusion device with the infusion pump comprises providing the first fluid through a first valve into the first chamber and providing the first fluid out of the first chamber through a second valve that is disposed on a moveable piston.

Concept 18. The method of Concept 17 or any other Concept, wherein displacing, by providing the second fluid, a portion of the first fluid in the first chamber into the second chamber comprises pushing, with the second fluid, the moveable piston and the second valve toward the first valve.

Concept 19. The method of Concept 18 or any other Concept, wherein displacing, by providing the second fluid, a portion of the first fluid in the first chamber into the second chamber further comprises pushing, with the moveable piston and the second valve, the portion of the first fluid through a third valve disposed between the first chamber and the second chamber.

Concept 20. The method of Concept 13 or any other Concept, wherein providing the second fluid into the first chamber from the port that is fluidly coupled to the first chamber comprises compressing a compressible member of the port to open a fluid pathway between a syringe and the first chamber and to close a fluid pathway between the first chamber and the output port.

Concept 21. The method of Concept 13 or any other Concept, further comprising:

receiving, with the infusion pump, a set identifier that identifies the micro-infusion device;

determining at least one property associated with the micro-infusion device based on the received set identifier; and operating the infusion pump, at least in part, based the determined at least one property.

Concept 22. The method of Concept 21 or any other Concept, wherein providing the second fluid from the first chamber through the output port with the infusion pump comprises operating one or more components of a pump cassette coupled to the infusion pump, wherein the pump cassette is a part of an IV set that includes the micro-infusion device, and wherein the pump cassette comprises a bar code or an RFID tag including the set identifier.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A method, comprising:

receiving, with an infusion pump, a set identifier that identifies a micro-infusion device comprising a first chamber disposed side by side and in parallel with a second chamber with each of the first chamber and the second chamber being linear;

determining at least one property associated with the micro-infusion device based on the received set identifier; and operating the infusion pump based on the determined at least one property to provide a first fluid and a second fluid through the first chamber and an output port of the micro-infusion device, wherein a portion of the first fluid in the first chamber is displaced into the second chamber of the micro-infusion device after the second fluid is received into the first chamber from a port directly coupled to the first chamber.

2. The method of claim 1, further comprising, operating the infusion pump to displace air in the second chamber through a vent in the second chamber with the portion of the first fluid.

3. The method of claim 2, further comprising, following the provision of the second fluid, operating the infusion pump to provide additional first fluid through the first chamber and the output port while the portion of the first fluid remains in the second chamber.

4. The method of claim 3, further comprising operating the infusion pump to remove the portion of the first fluid from the second chamber via a port in the second chamber.

5. The method of claim 1, wherein providing the first fluid through the first chamber of the micro-infusion device with the infusion pump comprises providing the first fluid through a first valve into the first chamber and to provide the first fluid out of the first chamber through a second valve that is disposed on a moveable piston.

6. The method of claim 5, wherein displacing, by providing the second fluid, the portion of the first fluid in the first chamber into the second chamber comprises pushing, with the second fluid, the moveable piston and the second valve toward the first valve.

7. The method of claim 6, wherein displacing, by providing the second fluid, the portion of the first fluid in the first chamber into the second chamber further comprises operating the infusion pump to push, with the moveable piston and the second valve, the portion of the first fluid through a third valve disposed between the first chamber and the second chamber.

8. The method of claim 1, wherein providing the second fluid into the first chamber from the port that is fluidly coupled to the first chamber comprises compressing a compressible member of the port to open a fluid pathway between a syringe and the first chamber and to close a fluid pathway between the first chamber and the output port.

9. The method of claim 1, wherein providing the second fluid from the first chamber through the output port with the infusion pump comprises operating one or more components of a pump cassette coupled to the infusion pump, wherein the pump cassette is a part of an IV set that includes the micro-infusion device, wherein the pump cassette comprises a bar code or an RFID tag including the set identifier.

10. A non-transitory computer-readable medium comprising instructions executable by at least one processor to cause an infusion pump to:

receive a set identifier that identifies a micro-infusion device comprising a first chamber disposed side by side and in parallel with a second chamber with each of the first chamber and the second chamber being linear;

determine at least one property associated with the micro-infusion device based on the received set identifier; and provide, based on the determined at least one property, a first fluid and a second fluid through the first chamber and an output port of the micro-infusion device; and displacing a portion of the first fluid in the first chamber into the second chamber of the micro-infusion device after the second fluid is received into the first chamber from a port directly coupled to the first chamber.

11. The non-transitory computer-readable medium of claim 10, wherein the at least one property is a volume of the first chamber, and wherein the non-transitory computer-readable medium further comprises instructions executable by at least one processor to cause the infusion pump to prime an infusion line coupled to the micro-infusion device based at least on the volume.

12. The non-transitory computer-readable medium of claim 10, wherein the at least one property is a volume of the first chamber, and wherein the non-transitory computer-readable medium further comprises instructions executable by at least one processor to cause the infusion pump to flush an infusion line coupled to the micro-infusion device based at least on the volume.

13. The non-transitory computer-readable medium of claim 10, wherein receiving the set identifier comprises receiving a wireless signal from a device attached to a portion of an infusion set including the micro-infusion device.

14. The non-transitory computer-readable medium of claim 10, wherein the non-transitory computer-readable medium further comprises instructions executable by at least one processor to cause the infusion pump to displace air in the second chamber through a vent in the second chamber with the portion of the first fluid.

15. The non-transitory computer-readable medium of claim 14, wherein the non-transitory computer-readable medium further comprises instructions executable by at least one processor to cause the infusion pump to provide additional first fluid through the first chamber and the output port while the portion of the first fluid remains in the second chamber, and to remove the portion of the first fluid from the second chamber via a port in the second chamber.

16. The non-transitory computer-readable medium of claim 10, wherein the non-transitory computer-readable medium further comprises instructions executable by at least one processor to cause the infusion pump to provide the first fluid through a first valve into the first chamber and to provide the first fluid out of the first chamber through a second valve that is disposed on a moveable piston.

17. The non-transitory computer-readable medium of claim 16, wherein the non-transitory computer-readable medium further comprises instructions executable by at least one processor to cause the infusion pump to push, with the second fluid, the moveable piston and the second valve toward the first valve.

18. The non-transitory computer-readable medium of claim 17, wherein the non-transitory computer-readable medium further comprises instructions executable by at least one processor to cause the infusion pump to push, with the moveable piston and the second valve, the portion of the first fluid through a third valve disposed between the first chamber and the second chamber.

19. The non-transitory computer-readable medium of claim 10, wherein the non-transitory computer-readable medium further comprises instructions executable by at least one processor to cause the infusion pump to compress a compressible member of the port to open a fluid pathway between a syringe and the first chamber and to close a fluid pathway between the first chamber and the output port.

20. The non-transitory computer-readable medium of claim 10, wherein the non-transitory computer-readable medium further comprises instructions executable by at least one processor to cause operation of one or more components of a pump cassette coupled to the infusion pump, wherein the pump cassette is a part of an IV set that includes the micro-infusion device, wherein the pump cassette comprises a bar code or an RFID tag including the set identifier.

* * * * *